United States Patent [19]

Kirmann

[11] Patent Number: Plant 6,012

[45] Date of Patent: Sep. 15, 1987

[54] GERANIUM PLANT NAMED MACY

[75] Inventor: Wolfgang Kirmann, Langenzersdorf, Austria

[73] Assignee: Mirko Vavra, Bisamberg, Austria

[21] Appl. No.: 810,674

[22] Filed: Dec. 19, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Macy having bright red-purple flower color, variegated with scarlet red; compact, self-branching growth habit; early flowering; good bud production at night temperatures up to 16° C., thus providing a long and continuous flowering period; and ease of propagation and good rooting habit.

2 Drawing Figures

The present invention comprises a new and distinct cultivar of geranium, botanically known as *Pelargonium domesticum,* and hereinafter referred to by the cultivar name Macy.

Macy is a product of a planned breeding program which had the objective of creating new geranium cultivars having compact growth habit, early flowering, good flower production, long flowering period, relatively small foliage and red-purple flower color.

Macy was originated from a hybridization made by applicant in a controlled breeding program in Bisamberg, Austria in 1980. The female parent was a cultivar designated as seedling 920/78 having red flower color, good flower production, medium growth habit and relatively large foliage. The male parent of Macy was a cultivar designated as seedling 123/79 having a compact growth habit, relatively small foliage and scarlet red flower color.

Macy was discovered and selected as one flowering plant within the progeny of the stated cross by applicant on Mar. 20, 1981 in a controlled environment in Bisamberg, Austria.

The first act of asexual reproduction of Macy was accomplished when vegetative cuttings were taken from the initial selection on Aug. 30, 1981 in a controlled environment in Bisamberg, Austria by a technician working under formulations established and supervised by Wolfgang Kirmann. Horticultural examination of selected units initiated in the spring of 1982 has demonstrated that the combination of characteristics as herein disclosed for Macy are firmly fixed and are retained through successive generations of asexual reproduction.

Macy has not been observed under all possible environmental conditions. The phenotype may vary significantly with variations in environment such as temperature, light intensity, and day length. The following observations, measurements and comparisons describe plants grown in Bisamberg, Austria under conditions which approximate those generally used in commercial practice.

The following traits have been repeatedly observed and are determined to be basic characteristics of Macy, which in combination distinguish this geranium as a new and distinct cultivar.

1. Bright red-purple flower color, variegated primarily near the throat with deep scarlet red.
2. Early flowering and long flowering period.

3. Dark green, small foliage.
4. Compact, self-branching growth habit, resulting in the setting of many buds.
5. Propagates well, with very good rooting habit.
6. Relatively small flower but prolific, producing a flower head that extends beyond the foliage.
7. Buds are produced under normal greenhouse conditions (5000 Lux for 16 hours per day) at 14°-16° C. This is well above the cooler temperatures required for previous *domesticum* varieties. In addition, plants flowered indoors can be transplanted outdoors and will continue blooming at night temperatures as high as 16° C. Known *domesticum* cultivars will produce buds outdoors only at night temperatures of 10° C. or lower.
8. Macy is unique with regard to the combined features of compactness, continuous flowering, floriferous habit, and red-purple flower color.

Of the many commercial cultivars known to the present inventor, the most similar in comparison to Macy is Fruhling, an unpatented but commercial cultivar. In comparison to Fruhling, Macy has a more compact growth habit, smaller foliage, better flower production, smaller petals and a more intense color.

The accompanying photographic drawings show typical flower and foliage characteristics of Macy, with colors being as true as possible with illustrations of this type.

Sheet 1 is a perspective view of a potted plant of Macy.

Sheet 2 is a black and white print showing the upper surface of immature and mature plants of Macy.

In the following description color references are made to The Royal Horticultural Society Colour Chart (R.H.S.). The color values were determined at 9:00 a.m. on May 23, 1985 under 35,000 Lux light intensity in a greenhouse at Hillscheid, Federal Republic of Germany.

CLASSIFICATION

Botanical: *Pelargonium domesticum.*

Commercial: Commonly referred to as a "Martha Washington" geranium, and having the cultivar name Macy.

INFLORESCENCE

A. Umbel:

*Average diameter.*—Relatively small, 85-95 mm.

*Peduncle length.*—Normal.

*Pedicel length.*—Normal.

B. Corolla:

*Average diameter.*—55–65 mm; highly floriferous habit results in the total inflorescence extending well beyond the edge of the foliage.

*Form.*—Five-seven petals.

*Color (general tonality from a distance of three meters).*—Bright red-purple with scarlet red variegation on the upper petals.

*Color (upper surface).*—63B, variegated with 45A.

C. Bud:

*Shape.*—Elongated.

*Color.*—Scarlet red.

D. Reproductive organs:

*Androecium.*—Yellow; 7–9 stamens.

*Gynoecium.*—Five to seven lobed stigma.

E. Spring flowering response period: Early.

G. Durability: Good.

PLANT

A. Foliage:

*Form.*—Zygomorphic with a nectar spur.

*Margin.*—Crenate to serrate and indented.

*Color (upper surface).*—Dark green.

*Tolerance of Botrytis and soil fungi.*—Good.

B. General appearance and form:

*Internode length.*—Short.

*Branching pattern.*—Excellent.

*Height.*—Compact.

I claim:

1. A new and distinct cultivar of geranium named Macy, as described and illustrated, and particularly characterized by its bright red-purple flower color, variegated with scarlet red; compact, self-branching growth habit; early flowering; good bud production at night temperatures up to 16° C., thus providing a long and continuous flowering period; and ease of propagation and good rooting habit.

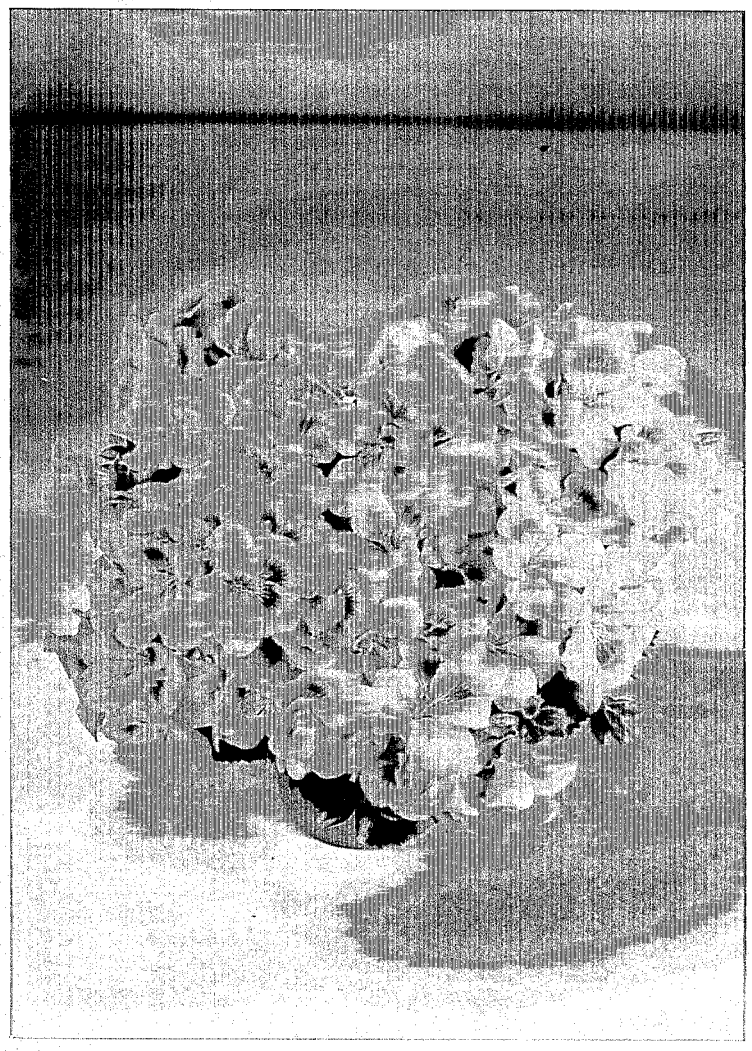

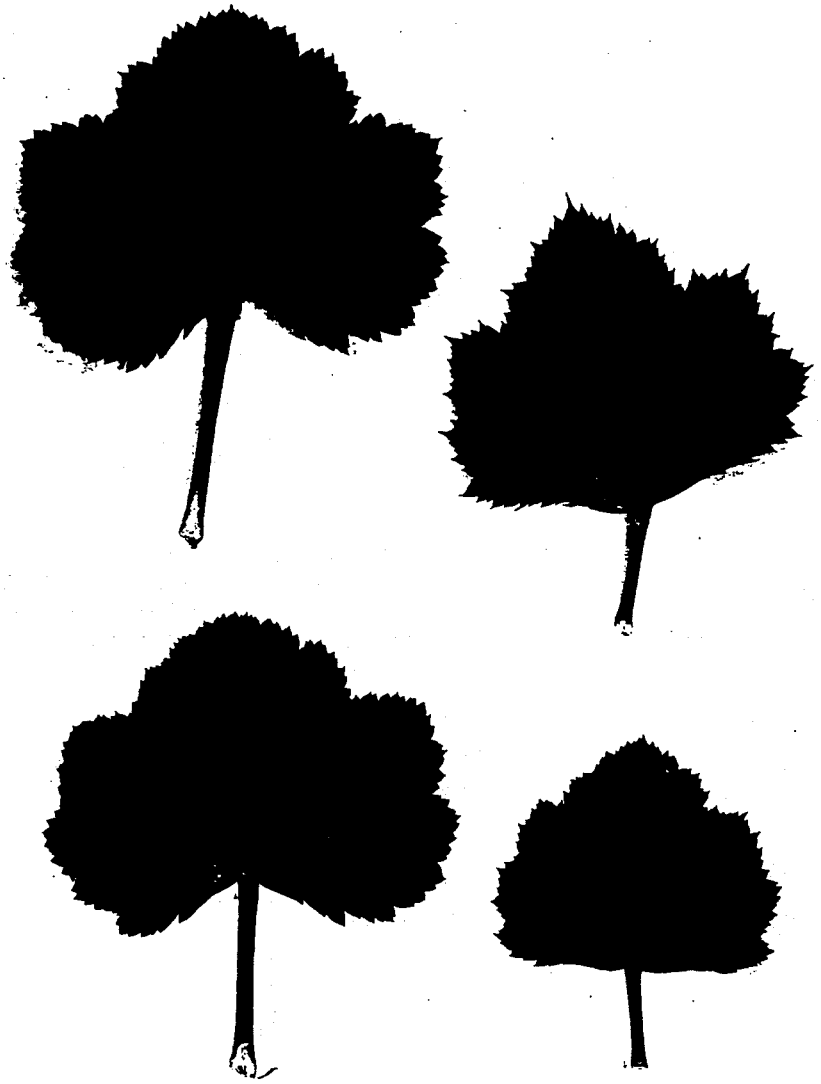

* * * * *